(12) United States Patent
Lawandy

(10) Patent No.: US 11,957,800 B2
(45) Date of Patent: Apr. 16, 2024

(54) HEAT TREATMENT OF BANKNOTES IN AN OXYGEN-FREE ENVIRONMENT

(71) Applicant: Spectra Systems Corporation, Providence, RI (US)

(72) Inventor: Nabil Lawandy, Saunderstown, RI (US)

(73) Assignee: Spectra Systems Corporation, Providence, RI (US)

( * ) Notice: Subject to any disclaimer, the term of this patent is extended or adjusted under 35 U.S.C. 154(b) by 431 days.

(21) Appl. No.: 17/322,017

(22) Filed: May 17, 2021

(65) Prior Publication Data

US 2022/0184243 A1 Jun. 16, 2022

Related U.S. Application Data

(62) Division of application No. 17/179,819, filed on Feb. 19, 2021, now Pat. No. 11,007,288.

(60) Provisional application No. 63/126,513, filed on Dec. 16, 2020.

(51) Int. Cl.
*A61L 2/04* (2006.01)
*A61L 2/20* (2006.01)

(52) U.S. Cl.
CPC .................. *A61L 2/04* (2013.01); *A61L 2/20* (2013.01); *A61L 2202/122* (2013.01); *A61L 2202/26* (2013.01)

(58) Field of Classification Search
CPC ........ A61L 2/04; A61L 2/20; A61L 2202/122; A61L 2202/26
See application file for complete search history.

(56) References Cited

U.S. PATENT DOCUMENTS

| 6,946,106 | B1 | 9/2005 | Masyada | |
|---|---|---|---|---|
| 8,961,702 | B2 | 2/2015 | Lawandy | |
| 11,007,288 | B1 | 5/2021 | Lawandy | |
| 2006/0278078 | A1* | 12/2006 | Holt | B01D 53/047 |
| | | | | 95/138 |
| 2009/0301679 | A1 | 12/2009 | Wetherell | |
| 2018/0028703 | A1* | 2/2018 | McLaughlin | A61B 50/34 |
| 2019/0291148 | A1 | 9/2019 | Lawandy | |

FOREIGN PATENT DOCUMENTS

| DE | 202016005870 U1 * | 3/2017 |
|---|---|---|
| JP | 2645944 B2 * | 8/1997 |

OTHER PUBLICATIONS

Derwent Abstract for DE 202016005870 U1 (Year: 2017).*

(Continued)

*Primary Examiner* — Sean E Conley
(74) *Attorney, Agent, or Firm* — Pryor Cashman LLP

(57) ABSTRACT

A method and associated apparatus for disinfecting at least one banknote, each banknote including a substrate, visual data, and a security feature, including disposing the at least one banknote in an oxygen-free environment, and exposing the at least one banknote to a temperature and for a duration sufficient to disinfect the at least one banknote and not compromise the security feature and the visual data, where to disinfect the at least one banknote includes to significantly deactivate, kill, or eliminate one or more pathogens from the at least one banknote.

18 Claims, 8 Drawing Sheets

N₂ Generation System

Banknote Heating Oven

(56) References Cited

OTHER PUBLICATIONS

English language machine translation for JP 2645944 A, Inventor: Takumi et al. (Year: 1997).*
International Search Report in PCT/US2021/063778 (dated Mar. 8, 2022).
Written Opinion of the International Searching Authority in PCT/US2021/063778 (dated Mar. 8, 2022).

* cited by examiner

FIG. 1

Table 1 Calculated D values (time taken to achieve a 90% reduction in titre) and half-life (time taken to achieve a 50% reduction in titre—in parentheses) for all surfaces at 20 °C, 30 °C and 40 °C

|  | D values (half-life) | | | Z value |
| --- | --- | --- | --- | --- |
|  | 20 °C—days | 30 °C—days | 40 °C – hours | (°C) |
| Stainless steel | 5.96 (1.80) | 1.74 (12.6 h) | 4.86 (1.5 h) | 13.62 |
| Polymer note | 6.85 (2.06) | 2.04 (14.7 h) | 4.78 (1.4 h) | 13.02 |
| Paper note | 9.13 (2.74) | 4.32 (32.7 h) | 5.39 (1.6 h) | 12.43 |
| Glass | 6.32 (1.90) | 1.45 (10.5 h) | 6.55 (2.0 h) | 14.65 |
| Cotton | 5.57 (1.68) | 1.65 (11.0 h) | – | 18.91 |
| Vinyl | 6.34 (1.91) | 1.40 (10.1 h) | 9.90 (3.0 h) | 16.86 |

HEAT TREATMENT OF BANKNOTES IN AN OXYGEN-FREE ENVIRONMENT

CROSS-REFERENCE TO RELATED APPLICATIONS

The present application is a divisional of U.S. non-provisional application Ser. No. 17/179,819, filed Feb. 19, 2021, which claims priority to U.S. provisional application Ser. No. 63/126,513, filed Dec. 16, 2020, the disclosures of which are incorporated herein by reference in their entirety.

TECHNICAL FIELD

The present invention relates to the heat treatment of banknotes in an oxygen-free environment. More particularly, the present invention relates to the inactivation of viruses and other pathogens on banknotes as a result of heat treatment in an oxygen-free environment, such as a nitrogen gas or inert gas environment.

BACKGROUND OF THE INVENTION

Since the outbreak of the COVID-19/SARS-CoV-2 virus and the ensuing global pandemic, there has been a great deal of activity related to methods of inactivating this virus and other viruses and pathogens on a variety of surfaces and personal protective equipment.

Important surfaces are found on banknotes, which are essentially two-surface structures and are commonly handled in the normal course of daily commercial transactions. Several methods have been proposed to handle pathogens on banknotes, including the use of supercritical $CO_2$, as taught in U.S. Pat. No. 9,610,619, and the heating of banknotes for extended periods of time in air atmospheres, as described in U.S. Pat. Nos. 6,946,106 and 5,626,822. The patents that describe methods involving heat and transport mechanisms require lower temperatures to avoid damaging the paper or polymer substrates and the attendant security features of banknotes, particularly fluorescent pigments. Such security features are an expensive aspect of the banknotes.

Studies by various groups have shown that the COVID-19/SARS-CoV-2 virus can last up to 28 days at a temperature of 20° C. on both polymer banknotes and paper banknotes. FIG. 1 provides data from the Australian Centre for Disease Preparedness [Riddell et al. Virology Journal, 2020] concerning inactivation rate coefficients for various surfaces. Based on this data, at a temperature of 200° C., a paper banknote would be sterilized ($Log_{10}$ drop of 6 orders of magnitude) in 2 hours. Previous inventions limit the temperatures to well under 100° C. to avoid damaging the banknotes. At the lower temperatures in these previous inventions, e.g., 40° C., a decrease of 6 orders of magnitude would require approximately three days for sterilization.

SUMMARY OF THE INVENTION

In general, in one aspect, the invention features a method for disinfecting at least one banknote, each banknote including a substrate, visual data, and a security feature, including disposing the at least one banknote in an oxygen-free environment, and exposing the at least one banknote to a temperature and for a duration sufficient to disinfect the at least one banknote and not compromise the security feature and the visual data, where to disinfect the at least one banknote includes to significantly deactivate, kill, or eliminate one or more pathogens from the at least one banknote.

Implementations of the invention may include one or more of the following features. The temperature may be in a range of 60° C. to 200° C. The duration may be in a range of 1 hour to 5 hours. The oxygen-free environment may be a nitrogen gas atmosphere or an inert gas atmosphere. The substrate may be a paper substrate or a polymer substrate. The at least one banknote may include a stack of banknotes bound together by a strap or shrink wrapping. The one or more pathogens may include COVID-19/SARS-CoV-2 virus, SARS-CoV-1 virus, MERS virus, Ebola virus, and bacteria. To significantly deactivate, kill, or eliminate one or more pathogens may include a greater than or equal to 6-log reduction in viral loading.

In general, in another aspect, the invention features an apparatus for disinfecting at least one banknote, each banknote including a substrate, visual data, and a security feature, including a unit configured to maintain an oxygen-free environment at a temperature and for a duration sufficient to disinfect the banknote and not compromise the security feature and the visual data, where to disinfect the at least one banknote includes to significantly deactivate, kill, or eliminate one or more pathogens from the at least one banknote.

Implementations of the invention may include one or more of the following features. The temperature may be in a range of 60° C. to 200° C. The duration may be in a range of 1 hour to 5 hours. The oxygen-free environment may be a nitrogen gas atmosphere. The apparatus may further include a nitrogen generation system configured to generate nitrogen gas from ambient air for use in the unit, and the nitrogen generation system may include a pressure swing adsorption nitrogen gas generator or a membrane separation nitrogen gas generator. The oxygen-free environment may be an inert gas atmosphere. The apparatus may further include a structure for holding the at least one banknote within the unit, and the structure for holding the at least one banknote may include a tray, a cart, or a tray disposed on a cart. The apparatus may further include one or more oxygen sensors disposed within the unit. The unit may be connected to or disposed within an ATM machine, a bank vault, or an armored vehicle.

In general, in another aspect, the invention features an apparatus for disinfecting at least one banknote, each banknote including a substrate, visual data, and a security feature, including an oxygen-free atmosphere generation device configured to generate an oxygen-free atmosphere, and a heating unit configured to receive and maintain the oxygen-free atmosphere at a temperature and for a duration sufficient to disinfect the banknote and not compromise the security feature and the visual data, where to disinfect the at least one banknote includes to significantly deactivate, kill, or eliminate one or more pathogens from the at least one banknote.

Implementations of the invention may include one or more of the following features. The oxygen-free atmosphere may be a nitrogen gas atmosphere, and the oxygen-free atmosphere generation device may include a pressure swing adsorption nitrogen gas generator or a membrane separation nitrogen gas generator.

BRIEF DESCRIPTION OF THE DRAWINGS

FIG. 1 shows data from the Australian Centre for Disease Preparedness [Riddell et al. Virology Journal, 2020] concerning inactivation rate coefficients for various surfaces;

DETAILED DESCRIPTION OF THE INVENTION

The present invention is directed to the use of oxygen-free environments to significantly accelerate the deactivation of viruses and other pathogens at high temperatures without causing damage to the paper or polymer banknotes, e.g., banknotes having paper or polymer substrates, and their attendant security features. Substances to be treated and/or inactivated include, but are not limited to, pathogens of COVID-19/SARS-CoV-2, SARS-CoV-1, MERS, Ebola, and bacteria.

Tests on various banknotes, including Rupees, Euros, and U.S. dollar bills, have shown that the elimination of oxygen allows these banknotes to be exposed to temperatures of 60° C.-200° C. for periods of 1-5 hours without damage to the substrate of the security features, such as security threads and fluorescent inks.

One aspect concerning the viability of treating banknotes using the methodology of the present invention is maintaining the integrity and usefulness of the important and costly public and machine-readable security features of the banknotes. Optical studies of the examined banknotes revealed improved results as to the quality or contrast of the printing after undergoing treatments of the present invention, such as flexographic, gravure and intaglio and optically variable inks, as compared to previously-known methods of treatment. Another feature of the present invention is that the security features on the banknotes are either totally unaffected or weakly diminished by the treatment process, such security features including one or more of magnetic inks, fluorescence of UV active features, holograms, metalized and de-metalized threads, optically variable inks, and the like.

Figure 2:
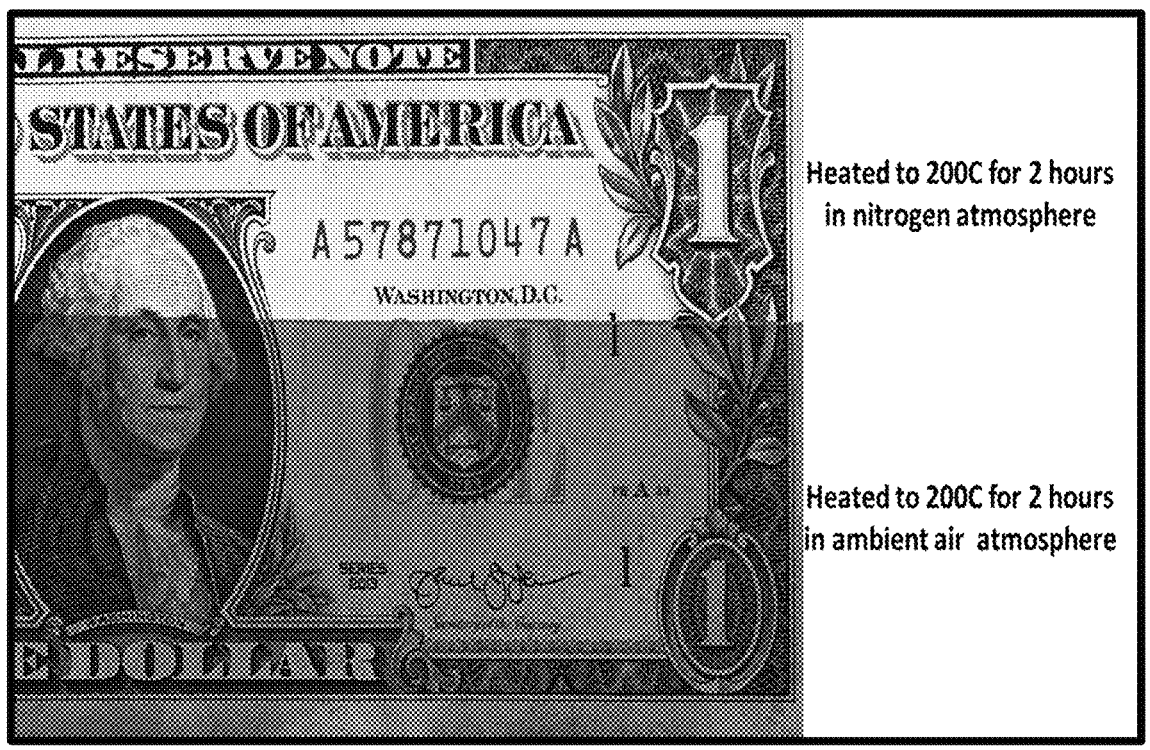
FIG. 2 shows a visual comparison of a U.S. $1 dollar bill heated at 200° C. for 2 hours in an ambient air atmosphere and in a nitrogen atmosphere.

FIG. 2 shows a U.S. $1 dollar bill heated at 200° C. for 2 hours in an ambient air atmosphere and in a nitrogen ($N_2$) atmosphere. Similar effects are obtained using other gases such as helium (He), argon (Ar), and xenon (Xe). As demonstrated by the visual comparison provided in FIG. 2, there is a greater efficacy associated with the present invention, as the lower half of the banknote exhibits severe oxidation in the ambient air atmosphere while the upper portion of the banknote, which was heated at the same temperature and for the same duration, remains intact.

Figure 3:
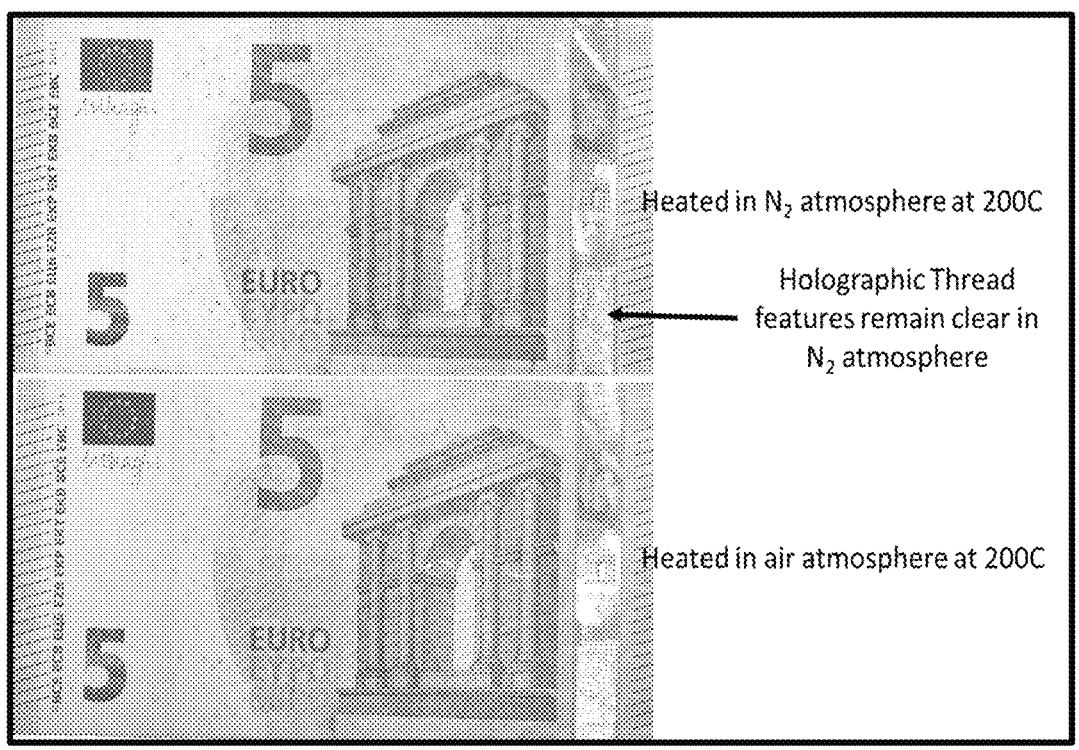
FIG. 3 shows a visual comparison of a 5 Euro banknote heated at 200° C. for 2 hours in an ambient air atmosphere and in a nitrogen atmosphere.

Experiments with Euro banknotes were also undertaken to examine the effects of heating in oxygen-free environment and in an ambient air environment on the holographic features of the banknotes. FIG. 3 shows a 5 Euro banknote heated at 200° C. for 2 hours in an ambient air atmosphere and in a nitrogen ($N_2$) atmosphere. As demonstrated by the visual comparison provided in FIG. 3, the security features (holographic thread) remained clear after treatment in the $N_2$ atmosphere, while after treatment in the ambient air atmosphere, there was noticeable degradation to the security features.

Figure 4:
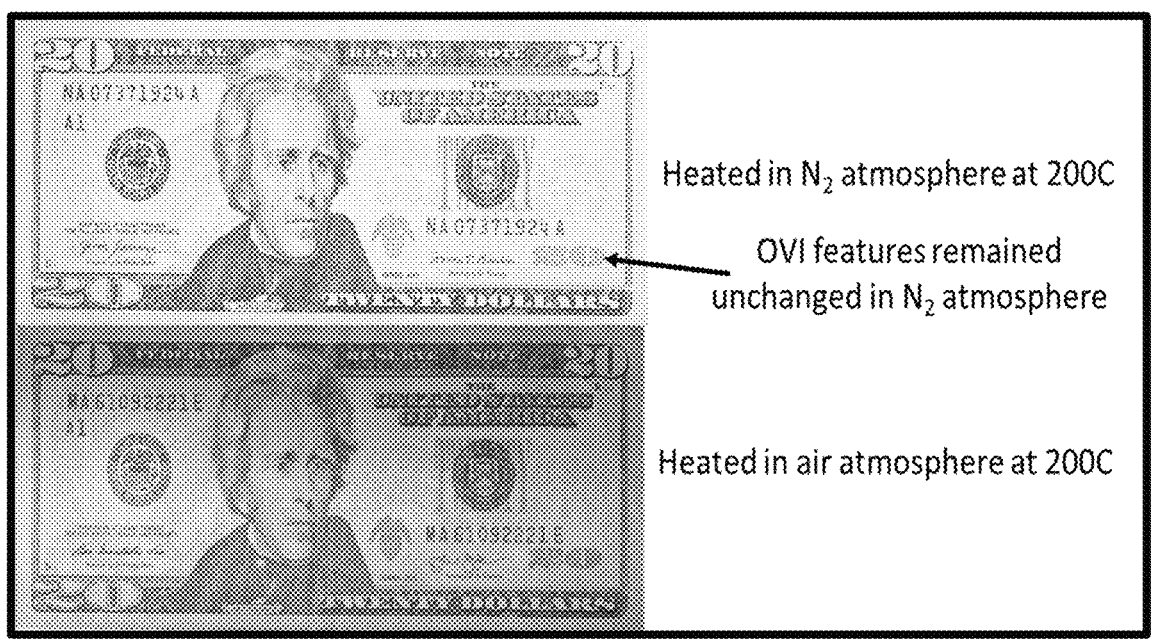
FIG. 4 shows a visual comparison of U.S. $20 dollar bills heated at 200° C. in an ambient air atmosphere and in a nitrogen atmosphere.

Similar experiments were undertaken with U.S. $20 dollar bills to investigate the effects of the heating in the different atmospheric conditions on the optically variable inks (OVI). FIG. 4 shows U.S. $20 dollar bills heated at 200° C. in an ambient air atmosphere and in a nitrogen ($N_2$) atmosphere. Similarly to FIG. 2, FIG. 4 demonstrates the browning of the bill treated in the ambient air atmosphere due to oxidation of the banknote in air. FIG. 4 also shows that the OVI features are unaffected by the treatment in the $N_2$ atmosphere.

Polymer banknotes were found to be capable of treatment at 120° C. in oxygen-free environments without sustaining damage, and accordingly such treatment for a duration of 5 hours would achieve a reduction of $Log_{10}$ of 6 in viral loading.

Figure 5:
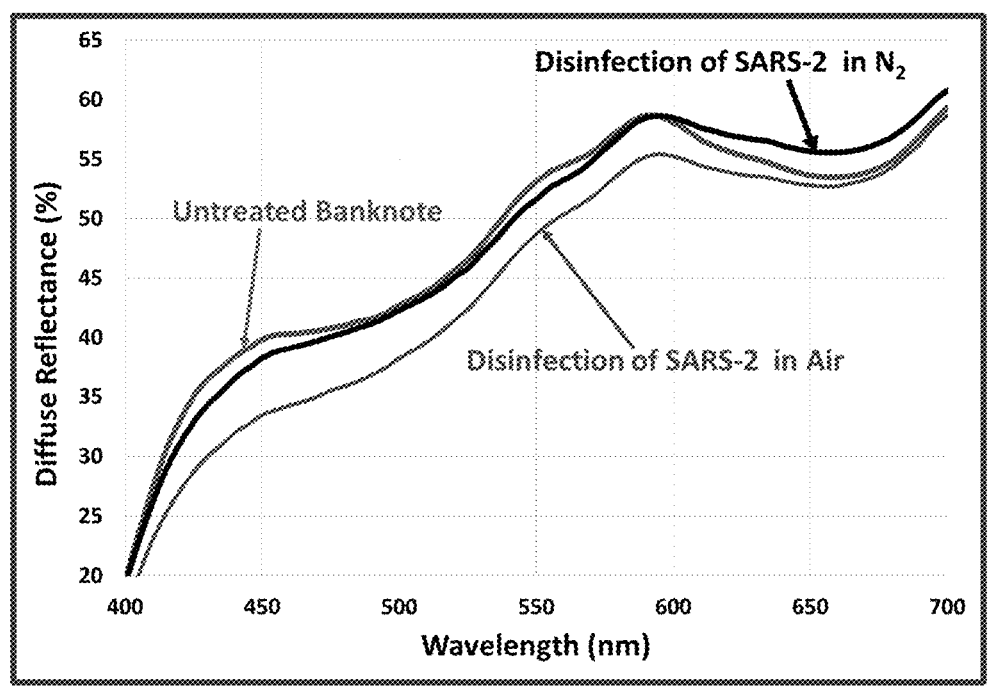
FIG. 5 shows diffuse reflectance comparisons of untreated banknotes, banknotes heat treated in an ambient air atmosphere, and banknotes heat treated in a nitrogen atmosphere.

FIG. 5 shows diffuse reflectance comparisons of untreated banknotes, banknotes treated in an ambient air atmosphere for COVID-19/SARS-CoV-2 disinfection, and banknotes treated in a nitrogen atmosphere for COVID-19/SARS-CoV-2 disinfection. As demonstrated by FIG. 5, physical integrity of the banknotes, including substrate, ink, and security features, remains intact after nitrogen atmosphere heat treatment and is superior to ambient air heat treatment. FIG. 5 provides diffuse reflectance measurements at banknote edges, watermarked regions, and other critical regions that establish the banknote substrate is not compromised for subsequent machine-readable fitness characterization.

Figure 6:
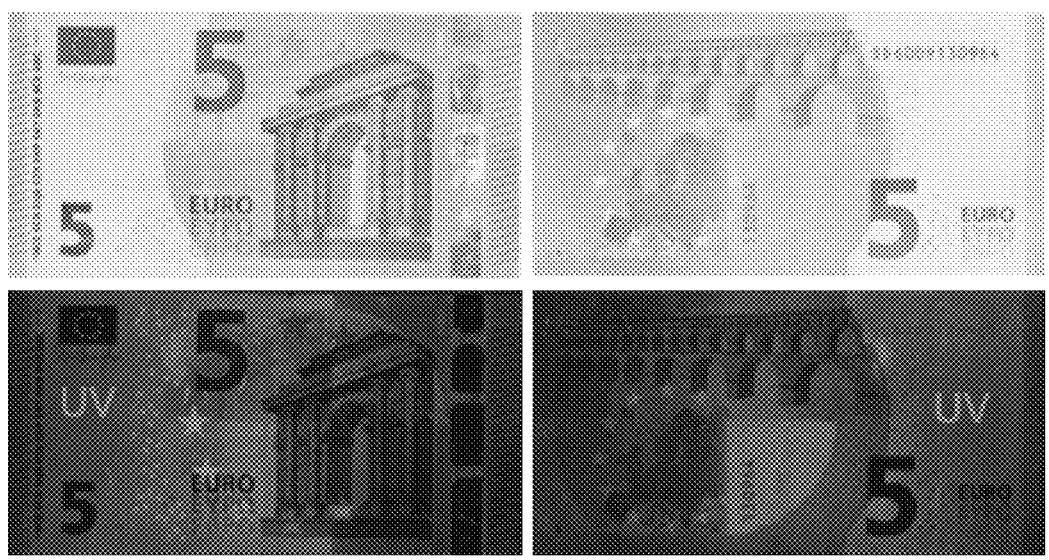
FIG. 6 shows several images of a U.S. $20 dollar bill after treatment according to one embodiment of the present invention.
Figure 7:
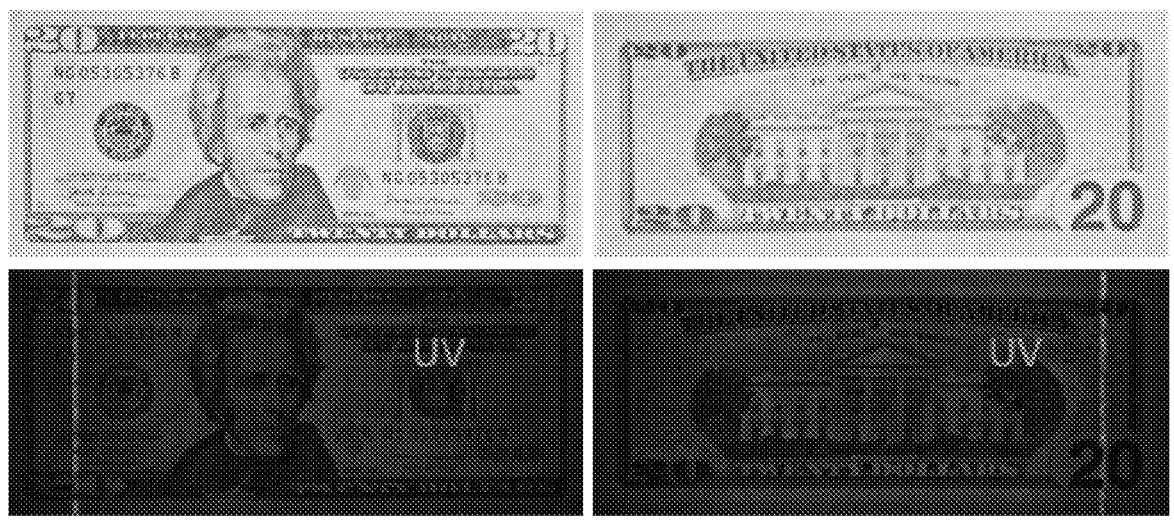
FIG. 7 shows several images of a 5 Euro banknote after treatment according to one embodiment of the present invention.

FIG. 6 shows a U.S. $20 dollar bill after a disinfection process of the present invention, namely an oxygen-free heat treatment of the banknote. Similarly, FIG. 7 shows a 5 Euro banknote after a disinfection process of the present invention, namely an oxygen-free heat treatment of the banknote. The images provided in FIGS. 6-7 demonstrate that the security features included in the banknotes, such as fluorescent, foil, security threads and fibers, and the print features of the banknotes remain intact.

Further aspects of the present invention include an apparatus for effectuating the described treatment, including a unit, e.g., an oven, capable of achieving a temperature of 300° C. for variable volumes up to several thousand liters, e.g., an 8 ft×8 ft×12 ft unit, and permitting the creation and maintenance of an oxygen-free environment through flow of nitrogen or an inert gas, e.g., helium, argon, xenon, etc. Such a large system could sterilize approximately 5,000,000 to 8,000,000 banknotes per hour, e.g., at 200° C. An apparatus of the present invention may be configured such that the banknotes are sterilized in straps and in bundles, such as in a manner typical of central bank operations. An apparatus of the present invention may include oxygen sensors within the enclosure or container to ensure that banknotes are not oxidized and to permit shutting off or deactivating the heating if oxygen leaks or an unacceptable level of oxygen, i.e., oxygen above a critical level, is detected. Relatedly, the apparatus may also include a cooling system configured to be activated based on oxygen presence or unacceptable level detection. An apparatus of the present invention may additionally include oxygen-free atmosphere generation devices, such as nitrogen generators using membrane separation and pressure swing adsorption for providing the desired nitrogen gas, in combination with the unit, e.g., oven. An apparatus of the present invention may be employed as part of, or in association with, an ATM machine, a bank vault, an armored vehicle, and the like, such that the banknotes can be sterilized in an oxygen-free environment, e.g, during bank closure hours, non-use or inactive periods, and overnight.

Figure 8:
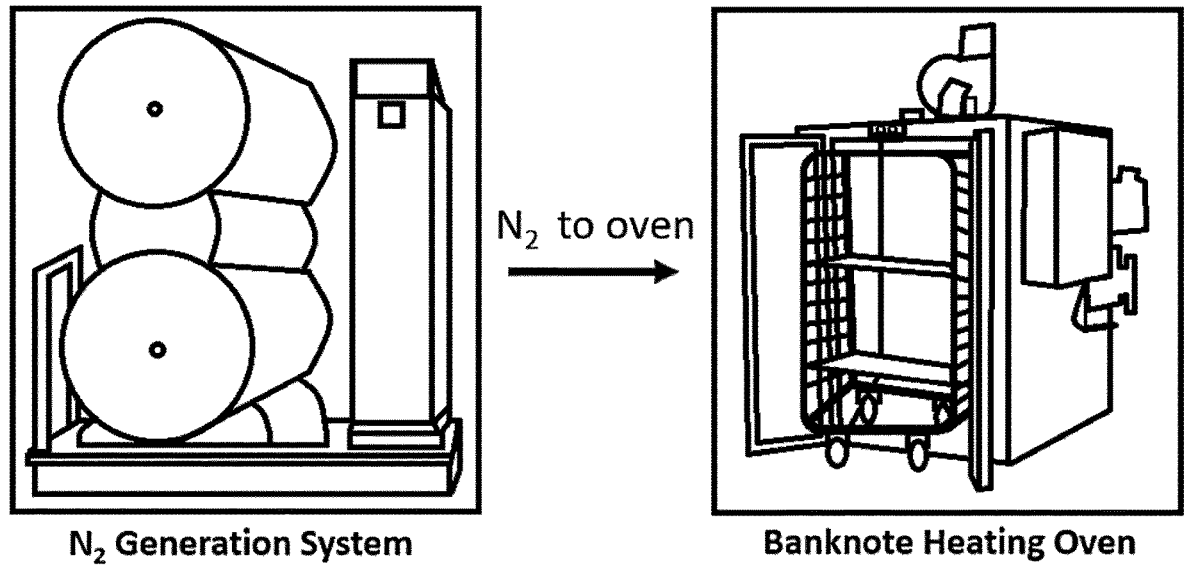
FIG. 8 shows a schematic diagram of a banknote disinfection apparatus according to one embodiment of the present invention.

FIG. 8 provides a schematic diagram of an apparatus according to one embodiment of the present invention, which includes a nitrogen generation system and a banknote heating oven, the nitrogen generation system generating nitrogen to be utilized in the banknote heating oven for its nitrogen atmosphere. The apparatus of FIG. 8 has the capacity to disinfect 4,000,000 to 6,000,000 banknotes in one hour. With this apparatus, banknotes may be treated in straps or in bundles, which may be wrapped in plastic shrink wrap or with a plastic or paper strap as is customary in the banknote handling and storage industry.

The nitrogen generation system may be or include a pressure swing adsorption nitrogen gas generator, which functions to extract oxygen from the ambient air and produce the nitrogen atmosphere for and within the banknote heating oven. The nitrogen generation system may provide for nitrogen gas having a purity of 98%, a flow rate of 1,500 scfh, and/or a delivery pressure of 90 psig. The associated air compressor may operate at 15 kW (or 20 hp).

The banknote heating oven may be or include a large scale oven unit, such as a walk-in cart oven. The banknote heating oven may include oxygen sensors (such as with associated alarms), purge valves, and timing controls. The interior dimensions of the heating portion of the oven may be 4'-6" W×10'-0" D×6'-0" H. A cart may be utilized in connection with the banknote heating oven, such that the banknotes are disposed on trays that are in turn disposed on the cart. The cart may have wheels, e.g., 4 wheels, for ease of inserting and removing the cart from the banknote heating oven. The banknote heating oven may have a thermal cycle of 250° C. (or 482° F.+/−15° F.) and/or a maximum oven temperature of 525° F. The total heat input may be 157 kW. The total oven atmosphere recirculation rate may be 9,500 cfm.

The embodiments and examples above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of this disclosure. The objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

What is claimed is:

1. A system for banknote disinfection, comprising:
at least one banknote, each banknote including a substrate, visual data, and a security feature;
a unit containing the at least one banknote and configured to maintain an oxygen-free environment at a temperature and for a duration sufficient to disinfect the at least one banknote and not compromise the security feature and the visual data of the at least one banknote; and
a structure holding the at least one banknote within the unit;
wherein to disinfect the at least one banknote includes to significantly deactivate, kill, or eliminate one or more pathogens from the at least one banknote.

2. The system of claim 1, wherein the temperature is in a range of 60° C. to 200° C.

3. The system of claim 1, wherein the duration is in a range of 1 hour to 5 hours.

4. The system of claim 1, wherein the oxygen-free environment is a nitrogen gas atmosphere.

5. The system of claim 4, further comprising:
a nitrogen generation system configured to generate nitrogen gas from ambient air for use in the unit.

6. The system of claim 5, wherein the nitrogen generation system includes a pressure swing adsorption nitrogen gas generator or a membrane separation nitrogen gas generator.

7. The system of claim 1, wherein the oxygen-free environment is an inert gas atmosphere.

8. The system of claim 1, wherein the structure holding the at least one banknote comprises a tray.

9. The system of claim 1, further comprising:
one or more oxygen sensors disposed within the unit.

10. The system of claim 1, wherein the unit is connected to or disposed within an ATM machine, a bank vault, or an armored vehicle.

11. A system for banknote disinfection, comprising:
at least one banknote, each banknote including a substrate, visual data, and a security feature;
an oxygen-free atmosphere generation device configured to generate an oxygen-free atmosphere;
a heating unit containing the at least one banknote and configured to receive and maintain the oxygen-free atmosphere at a temperature and for a duration sufficient to disinfect the at least one banknote and not compromise the security feature and the visual data of the at least one banknote; and
a structure holding the at least one banknote within the heating unit;
wherein to disinfect the at least one banknote includes to significantly deactivate, kill, or eliminate one or more pathogens from the at least one banknote.

12. The system of claim 11, wherein the oxygen-free atmosphere is a nitrogen gas atmosphere.

13. The system of claim 12, wherein the oxygen-free atmosphere generation device includes a pressure swing adsorption nitrogen gas generator or a membrane separation nitrogen gas generator.

14. The system of claim 1, wherein the structure holding the at least one banknote comprises a cart.

15. The system of claim 1, wherein the structure holding the at least one banknote comprises a tray disposed on a cart.

16. The system of claim 11, wherein the structure holding the at least one banknote comprises a tray.

17. The system of claim 11, wherein the structure holding the at least one banknote comprises a cart.

18. The system of claim 11, wherein the structure holding the at least one banknote comprises a tray disposed on a cart.

* * * * *